(12) United States Patent
Eidenschink et al.

(10) Patent No.: US 7,794,472 B2
(45) Date of Patent: Sep. 14, 2010

(54) SINGLE WIRE INTRAVASCULAR FILTER

(75) Inventors: Tracee E. J. Eidenschink, Wayzata, MN (US); Gordon Brooks, Lynnfield, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 584 days.

(21) Appl. No.: 10/916,114

(22) Filed: Aug. 11, 2004

(65) Prior Publication Data
US 2006/0036279 A1 Feb. 16, 2006

(51) Int. Cl.
A61M 29/00 (2006.01)
(52) U.S. Cl. .................................................. 606/200
(58) Field of Classification Search ................ 606/200, 606/108, 198; 128/830, 831, 833
See application file for complete search history.

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,683,904 A | 8/1972 | Forster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,447,227 A | 5/1984 | Kotsanis | |
| 4,580,568 A | 4/1986 | Gianturco | |
| 4,590,938 A | 5/1986 | Segura et al. | |
| 4,619,246 A | 10/1986 | Molgaard-Nielsen et al. | |
| 4,631,052 A | 12/1986 | Kensey | |
| 4,643,184 A | 2/1987 | Mobin-Uddin | |
| 4,650,466 A | 3/1987 | Luther | |
| 4,662,885 A | 5/1987 | DiPisa, Jr. | |
| 4,705,517 A | 11/1987 | DiPisa, Jr. | |
| 4,706,671 A | 11/1987 | Weinrib | |
| 4,723,549 A | 2/1988 | Wholey et al. | |
| 4,727,873 A | 3/1988 | Mobin-Uddin | |

(Continued)

FOREIGN PATENT DOCUMENTS

DE 28 21 048 7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Darwin P Erezo
*Assistant Examiner*—Melanie Tyson
(74) *Attorney, Agent, or Firm*—Crompton, Seager & Tufte LLC

(57) ABSTRACT

Single-wire intravascular filters for use in filtering blood clots within the body are disclosed. An intravascular filter in accordance with an illustrative embodiment of the present invention can include a single filter wire defining a first end section, a second end section, and one or more filter loops adapted to collect blood clots contained within a blood vessel. Each of the filter loops can be configured to slope outwardly at an angle away from a central longitudinal axis of the filter to form a conical-shaped structure having an apex section and a base section.

11 Claims, 8 Drawing Sheets

U.S. PATENT DOCUMENTS

| | | |
|---|---|---|
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,793,348 A | 12/1988 | Palmaz |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,817,600 A | 4/1989 | Herms et al. |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Gifford, III et al. |
| 4,950,277 A | 8/1990 | Farr |
| 4,955,895 A | 9/1990 | Sugiyama et al. |
| 4,957,482 A | 9/1990 | Shiber |
| 4,957,501 A | 9/1990 | Lahille et al. |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,059,204 A | 10/1991 | Lawson et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,418 A | 4/1992 | Lefebvre |
| 5,108,419 A | 4/1992 | Reger et al. |
| 5,133,733 A | 7/1992 | Resmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,217,484 A | 6/1993 | Marks |
| 5,224,953 A | 7/1993 | Morgentaler |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,484 A | 7/1994 | Gunther |
| 5,330,500 A | 7/1994 | Song |
| 5,344,427 A | 9/1994 | Cottenceau et al. |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazerus |
| 5,405,377 A | 4/1995 | Cragg |
| 5,409,454 A | 4/1995 | Fischell et al. |
| 5,413,586 A | 5/1995 | Dibie et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,531,788 A * | 7/1996 | Dibie et al. ............... 623/11.11 |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vorwerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,725,550 A | 3/1998 | Nadal |
| 5,728,066 A | 3/1998 | Daneshvar |
| 5,746,758 A | 5/1998 | Nordgren et al. |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,398 A | 4/1999 | Wensel et al. |
| 5,895,399 A | 4/1999 | Barbut et al. |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky et al. |

| | | | | | | |
|---|---|---|---|---|---|---|
| 5,925,060 | A | 7/1999 | Forber | 6,344,049 B1 | 2/2002 | Levinson et al. |
| 5,925,062 | A | 7/1999 | Purdy | 6,383,205 B1 | 5/2002 | Samson et al. |
| 5,925,063 | A | 7/1999 | Khosravi | 6,443,972 B1 | 9/2002 | Bosma et al. |
| 5,928,203 | A | 7/1999 | Davey et al. | 6,506,205 B2 | 1/2003 | Goldberg et al. |
| 5,928,218 | A | 7/1999 | Gelbfish | 6,551,342 B1 | 4/2003 | Shen et al. |
| 5,934,284 | A | 8/1999 | Plaia et al. | 6,562,058 B2 | 5/2003 | Seguin et al. |
| 5,935,139 | A | 8/1999 | Bates | 6,582,447 B1 | 6/2003 | Patel et al. |
| 5,938,645 | A | 8/1999 | Gordon | 6,623,506 B2 | 9/2003 | McGuckin, Jr. et al. |
| 5,941,869 | A | 8/1999 | Patterson et al. | 6,652,558 B2 | 11/2003 | Patel et al. |
| 5,941,896 | A | 8/1999 | Kerr | 6,689,150 B1 * | 2/2004 | VanTassel et al. ............ 606/200 |
| 5,947,995 | A | 9/1999 | Samuels | 2002/0010481 A1* | 1/2002 | Jayaraman .................. 606/151 |
| 5,951,585 | A | 9/1999 | Cathcart et al. | 2002/0052626 A1* | 5/2002 | Gilson et al. ................. 606/200 |
| 5,954,745 | A | 9/1999 | Gertler et al. | 2002/0138097 A1 | 9/2002 | Ostrovsky et al. |
| 5,968,071 | A * | 10/1999 | Chevillon et al. ............ 606/200 | 2003/0139765 A1* | 7/2003 | Patel et al. ................... 606/200 |
| 5,976,172 | A | 11/1999 | Homsma et al. | 2003/0163159 A1 | 8/2003 | Patel et al. |
| 5,980,555 | A | 11/1999 | Barbut et al. | 2004/0116959 A1* | 6/2004 | McGuckin et al. .......... 606/200 |
| 5,989,210 | A | 11/1999 | Morris et al. | 2005/0004596 A1* | 1/2005 | McGuckin et al. .......... 606/200 |
| 5,989,271 | A | 11/1999 | Bonnette et al. | 2005/0251197 A1* | 11/2005 | Hensley et al. .............. 606/200 |
| 5,989,281 | A | 11/1999 | Barbut et al. | | | |
| 5,993,469 | A | 11/1999 | McKenzie et al. | | | |

FOREIGN PATENT DOCUMENTS

| | | |
|---|---|---|
| 5,997,557 A | 12/1999 Barbut et al. | |
| 6,001,118 A | 12/1999 Daniel et al. | DE 34 17 738 11/1985 |
| 6,007,557 A | 12/1999 Ambrisco et al. | DE 40 30 998 A1 10/1990 |
| 6,010,522 A | 1/2000 Barbut et al. | EP 0 200 688 11/1986 |
| 6,013,085 A | 1/2000 Howard | EP 0 293 605 A1 12/1988 |
| 6,027,520 A | 2/2000 Tsugita et al. | EP 0 411 118 A1 2/1991 |
| 6,042,598 A | 3/2000 Tsugita et al. | EP 0 427 429 A2 5/1991 |
| 6,051,014 A | 4/2000 Jang | EP 0 437 121 B1 7/1991 |
| 6,051,015 A | 4/2000 Maahs | EP 0 472 334 A1 2/1992 |
| 6,053,932 A | 4/2000 Daniel et al. | EP 0 472 368 A2 2/1992 |
| 6,059,814 A | 5/2000 Ladd | EP 0 533 511 A1 3/1993 |
| 6,066,149 A | 5/2000 Samson et al. | EP 0 655 228 A1 11/1994 |
| 6,066,158 A | 5/2000 Engelson et al. | EP 0 686 379 A2 6/1995 |
| 6,068,645 A | 5/2000 Tu | EP 0 696 447 A2 2/1996 |
| 6,080,178 A | 6/2000 Meglin | EP 0 737 450 A1 10/1996 |
| 6,086,605 A | 7/2000 Barbut et al. | EP 0 743 046 A1 11/1996 |
| 6,117,154 A | 9/2000 Barbut et al. | EP 0 759 287 A1 2/1997 |
| 6,129,739 A | 10/2000 Khosravi | EP 0 771 549 A2 5/1997 |
| 6,136,016 A | 10/2000 Barbut et al. | EP 0 784 988 A1 7/1997 |
| 6,142,987 A | 11/2000 Tsugita | EP 0 852 132 A1 7/1998 |
| 6,152,946 A | 11/2000 Broome et al. | EP 0 934 729 8/1999 |
| 6,165,200 A | 12/2000 Tsugita et al. | FR 2 580 504 10/1986 |
| 6,168,579 B1 | 1/2001 Tsugita | FR 2 643 250 A1 8/1990 |
| 6,171,327 B1 | 1/2001 Daniel et al. | FR 2 666 980 3/1992 |
| 6,171,328 B1 | 1/2001 Addis | FR 2 768 326 A1 3/1999 |
| 6,179,851 B1 | 1/2001 Barbut et al. | GB 2 020 557 B 1/1983 |
| 6,179,859 B1 | 1/2001 Bates et al. | JP 8-187294 A 7/1996 |
| 6,203,561 B1 | 3/2001 Ramee et al. | SU 764684 9/1980 |
| 6,206,868 B1 | 3/2001 Parodi | WO WO 88/09683 12/1988 |
| 6,214,025 B1 | 4/2001 Thistle et al. | WO WO 92/03097 3/1992 |
| 6,214,026 B1 | 4/2001 Lepak et al. | WO WO 94/14389 7/1994 |
| 6,221,006 B1 | 4/2001 Dubrul et al. | WO WO 94/24946 11/1994 |
| 6,224,620 B1 | 5/2001 Maahs | WO WO 96/01591 1/1996 |
| 6,231,544 B1 | 5/2001 Tsugita et al. | WO WO 96/10375 4/1996 |
| 6,231,589 B1 * | 5/2001 Wessman et al. ............ 606/200 | WO WO 96/19941 7/1996 |
| 6,235,044 B1 | 5/2001 Root et al. | WO WO 96/23441 8/1996 |
| 6,235,045 B1 | 5/2001 Barbut et al. | WO WO 96/33677 10/1996 |
| 6,238,412 B1 | 5/2001 Dubrul et al. | WO WO 97/17100 5/1997 |
| 6,245,087 B1 | 6/2001 Addis | WO WO 97/27808 8/1997 |
| 6,245,088 B1 | 6/2001 Lowery | WO WO 97/42879 11/1997 |
| 6,245,089 B1 | 6/2001 Daniel et al. | WO WO 98/02084 1/1998 |
| 6,258,115 B1 | 7/2001 Dubrul | WO WO 98/02112 1/1998 |
| 6,264,663 B1 | 7/2001 Cano | WO WO 98/23322 6/1998 |
| 6,264,672 B1 | 7/2001 Fisher | WO WO 98/33443 8/1998 |
| 6,270,513 B1 | 8/2001 Tsugita et al. | WO WO 98/34673 8/1998 |
| 6,277,138 B1 | 8/2001 Levinson et al. | WO WO 98/36786 8/1998 |
| 6,277,139 B1 | 8/2001 Levinson et al. | WO WO 98/38920 9/1998 |
| 6,280,413 B1 | 8/2001 Clark et al. | WO WO 98/38929 9/1998 |
| 6,287,321 B1 | 9/2001 Jang | WO WO 98/39046 9/1998 |
| 6,290,710 B1 | 9/2001 Cryer et al. | WO WO 98/39053 9/1998 |
| 6,309,399 B1 | 10/2001 Barbut et al. | WO WO 98/46297 10/1998 |
| 6,319,268 B1 | 11/2001 Ambrisco et al. | WO WO 98/47447 10/1998 |
| 6,331,183 B1 | 12/2001 Suon | WO WO 98/49952 11/1998 |

| | | |
|---|---|---|
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8 (E):25E-30E (1996).

* cited by examiner

SINGLE WIRE INTRAVASCULAR FILTER

FIELD

The present invention relates generally to medial devices. More specifically, the present invention pertains to intravascular filters for use in filtering blood clots within a blood vessel.

BACKGROUND

Intravascular filters are used in combination with other thrombolytic agents to treat pulmonary embolism occurring within a patient. Such devices are typically inserted intravenously into a target location of the body (e.g. an artery or vein), and function by capturing blood clots (emboli) contained in the blood stream before they can reach the heart and/or lungs and cause permanent damage to the body. In the treatment of Deep Vein Thrombosis (DVT), for example, such filters can be placed in the inferior vena cava to prevent further blood clotting in the large veins of the lower body. Placement of the filter is typically accomplished percutaneously via the femoral arteries or the jugular vein using a local anesthetic, or by performing a laparotomy with the patient under general anesthesia.

SUMMARY

The present invention relates to intravascular filters for use in filtering blood clots within a blood vessel. An intravascular filter in accordance with an illustrative embodiment of the present invention comprises a single filter wire defining a first end section, a second end section, and one or more filter loops adapted to collect blood clots contained within a blood vessel. Each of the filter loops may slope outwardly at an angle away from a central longitudinal axis of the intravascular filter, forming a conical-shaped structure having an apex section and a base section. The filter loops may have an open-loop configuration defining an opening through which blood can flow through the filter substantially unimpeded. The configuration of the filter loops, including the size of the openings, can be altered to modify the performance characteristics of the intravascular filter, as desired. During deployment, the base section of the intravascular filter can be configured to engage the inner wall of the blood vessel, preventing the intravascular filter from migrating downstream in the blood vessel. In certain embodiments, an anchoring member coupled to one or more of the filter loops can be used to further secure the intravascular filter to the inner wall of the blood vessel, if desired.

Illustrative systems and methods for retrieving single-wire intravascular devices are also described herein. An illustrative method of retrieving an intravascular filter disposed within a patient's blood vessel may comprise the steps of providing a retrieval device including an elongated member having a proximal section and a distal section, inserting the distal section of retrieval device into the patient's vasculature and advancing the retrieval device to the site of the intravascular filter, coupling the retrieval device to the intravascular filter, inserting a retrieval sheath or catheter into the patient's vasculature and advancing the retrieval sheath or catheter to the site of the intravascular filter, loading the intravascular filter into an interior lumen of the retrieval sheath or catheter, and then removing the intravascular filter from the patient's body.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
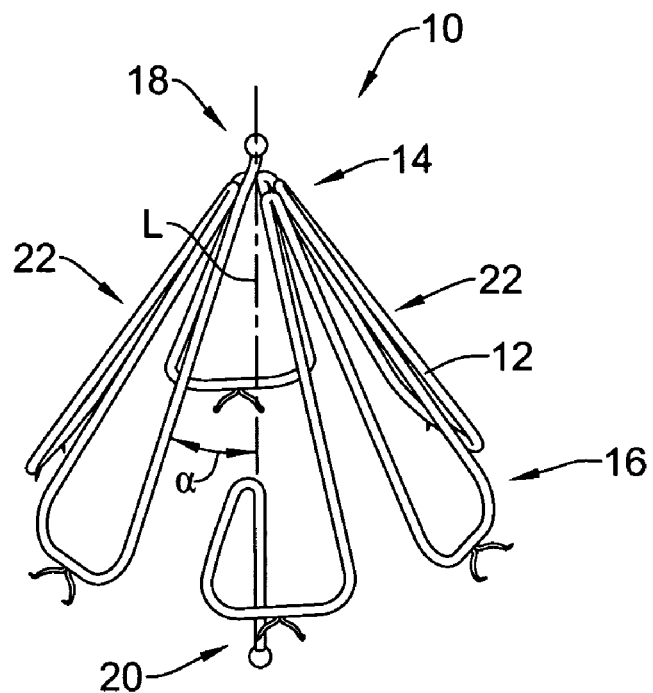
FIG. 1 is a perspective view of a single-wire intravascular filter in accordance with an illustrative embodiment of the present invention.

FIG. 1 is a perspective view of a single-wire intravascular filter 10 in accordance with an illustrative embodiment of the present invention. Intravascular filter 10, illustratively a vena cava filter, includes a single filter wire 12 forming a substantially conical-shaped structure having an apex section 14, a base section 16, and a central longitudinal axis L. While a conical-shaped structure is specifically depicted in the embodiment of FIG. 1, it should be understood that the intravascular filter 10 may assume other configurations, if desired. In one alternative embodiment, for example, the filter wire 12 can be configured to form a bell-shaped structure.

The filter wire 12 may extend from a first end section 18 located at or near the apex section 14 of the intravascular filter 10 to a second end section 20 located at or near the base section 16 of the intravascular filter 10. In certain embodiments, the first end section 18 of the filter wire 12 may terminate at a location proximally of the apex section 14, whereas the second end section 20 of the filter wire 12 may terminate at a location distally of the base section 16. In use, the first and second end sections 18,20 of the filter wire 12 can be configured to permit the intravascular filter 10 to be retrieved from the patient's body using either a jugular approach (i.e. via the jugular vein) or a femoral approach (i.e. via one of the femoral arteries).

As can be further seen in FIG. 1, the filter wire 12 may further define a number of open-ended filter loops 22, each of which can be used to collect blood clots or other emboli within the bloodstream. The filter loops 22, which are described in greater detail herein with respect to FIG. 2, can be biased to slope outwardly at an angle α away from the central axis L of the intravascular filter 10, causing the filter loops 22 to exert a radial force on the inner wall of the blood vessel during deployment. In some embodiments, each of the filter loops 22 can be configured to slope outwardly at the same angle α, providing a degree of radial symmetry to the intravascular filter 10. In other embodiments, the filter loops 22 can be configured to slope outwardly at differing angles α, providing asymmetry to the intravascular filter 10 that can be used, for example, to facilitate insertion of the device in blood vessels having an oval shape. In some embodiments, the filter wire 12 can have a substantially vertical orientation (i.e. α 45°) to promote clot collection and lysing at or near the apex section 14 of the intravascular filter 10 where the flow of blood is typically the greatest.

The filter wire 12 can be formed from a suitably flexible material that permits the intravascular filter 10 to be radially compressed into the interior lumen of a delivery sheath or catheter while regaining its original shape when deployed within the blood vessel. In certain embodiments, the filter wire 12 may be formed from a biocompatible metal such as titanium, platinum, tantalum, tungsten, gold, and/or stainless steel. In at least some embodiments, the filter wire 12 can be formed from a superelastic material such as a nickel-titanium alloy (Nitinol), which can be configured to withstand significant stresses without imparting a residual strain to the material. The use of superelastic materials may, in certain circumstances, permit the intravascular filter 10 to be loaded into smaller sized delivery devices without sacrificing the performance characteristics desired in the filter. The shape-memory properties exhibited by many superelastic materials can also be exploited to permit the filter wire 12 to assume a desired shape at a particular temperature or temperature range. In certain embodiments, for example, the intravascular filter 10 can be configured to revert from a substantially straight configuration to a conical-shaped configuration when deployed within the body, allowing the intravascular filter 10 to assume a relatively low profile within a catheter or sheath.

The dimensions and shape of the filter wire 12 employed can also be selected to impart a desired flexibility to the intravascular filter 10. If, for example, a greater amount of flexibility is desired, the filter wire 12 employed can be constructed from wire having a relatively large gauge. Conversely, if a lesser amount of flexibility is desired, the filter wire 12 can be constructed from wire having a relatively small gauge. While the illustrative filter wire 12 depicted in FIG. 1 has a substantially round transverse cross-section, it should be understood that filter wire 12 may assume other shapes (e.g. rectangular, oval, etc.), as desired.

Figure 2:
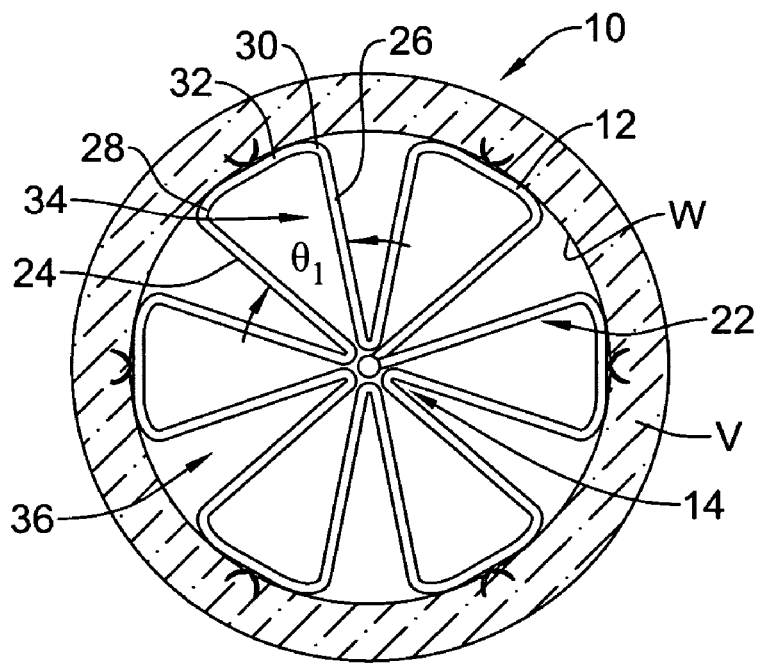
FIG. 2 is a top view showing the illustrative intravascular filter of FIG. 1 disposed within a blood vessel.

FIG. 2 is a top view showing the illustrative intravascular filter 10 of FIG. 1 disposed within a blood vessel V. As can be seen in FIG. 2, each of the filter loops 22 may include a first section 24 and second section 26, each of which extend outwardly away from the apex section 14 of the intravascular filter 10 in a direction towards the inner wall W of the blood vessel V. At locations 28 and 30, respectively, the first and second sections 24,26 of the filter loop 22 bend and orient in a direction aligned radially with the inner wall W of the blood vessel V, forming a third section 32 of the filter loop 22 configured to secure to the inner wall W of the blood vessel V. Together, the first, second, and third sections 24,26,32 of the filter loop 22 define an opening 34 through which blood can flow through the intravascular filter 10 substantially unimpeded.

As can be further seen in FIG. 2, the first and second sections 24,26 of each filter loop 22 can diverge from each other at an angle $\theta_1$ such that the opening 34 is greater towards the outer periphery of the intravascular filter 10 than at the apex section 14 thereof. In the illustrative embodiment depicted in FIG. 2, the filter loops 22 are shown having a relatively wide configuration (i.e. having a relatively large angle $\theta_1$), with the space 36 between each adjacent filter loop 22 being relatively small in comparison to the opening 34 defined by the filter loop 22.

The number and configuration of the filter loops 22 can be altered to change the performance characteristics of the intravascular filter 10 in a desired manner. In certain embodiments, for example, the angle $\theta_1$ at which the first and second sections 24,26 diverge from each other can be made larger to increase the exposed surface area of the intravascular filter 10. Conversely, the angle $\theta_1$ at which the first and second sections 24,26 diverge from each other can be lessened to decrease the exposed surface area of the intravascular filter 10. Moreover, while six filter loops 22 are specifically depicted in the embodiment of FIGS. 1-2, the number of filter loops 22 can also be increased or decreased to alter the performance characteristics of the intravascular filter 10.

The configuration of the filter loops 22 can also be varied depending on the particular dimensions of the blood vessel in which the intravascular filter 10 is to be implanted. In applications involving the inferior vena cava, for example, the filter loops 22 can be configured to form a base section 16 having a diameter of about 18 to 32 mm, which is the normal range for the human inferior vena cava. The dimensions and orientation of the filter loops 22 can vary, however, for use in other locations of the body such as the coronary arteries or the peripheral vasculature.

Figure 3:
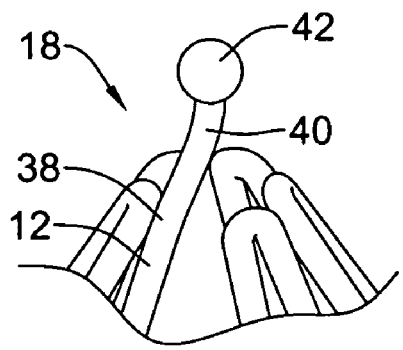
FIG. 3 is an enlarged view showing the first end section of the filter wire of FIG. 1 in greater detail.

FIG. 3 is an enlarged view showing the first end section 18 of the filter wire 12 of FIG. 1 in greater detail. As can be seen in FIG. 3, the first end section 18 may extend upwardly from an extended section 38 of one of the filter loops 22 wherein the filter wire 12 bends at location 40 and orients in an upward direction substantially collinear with the central longitudinal axis L of the intravascular filter 10. In the illustrative embodiment depicted, the first end section 18 terminates at a rounded bead 42, which, as described in greater detail herein with respect to FIGS. 10-13, can be used in conjunction with a retrieval device to retrieve the intravascular filter 10 from the blood vessel via a jugular approach.

Figure 4:
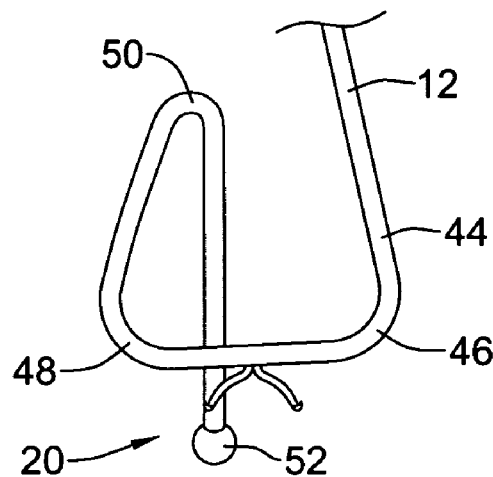
FIG. 4 is an enlarged view showing the second end section of the filter wire of FIG. 1 in greater detail.

In similar fashion, and as further shown in the enlarged view of FIG. 4, the second end section 20 of the filter wire 12 may extend downwardly from an extended portion 44 of one of the filter loops 22 wherein the filter wire 12 bends at locations 46,48,50 and orients in a downward direction substantially collinear with the central longitudinal axis L of the intravascular filter 10. As with the first end section 18, the second end section 20 may terminate at a rounded bead 52, which can be similarly used in conjunction with a retrieval device to retrieve the intravascular filter 10 via a femoral approach.

Figure 5:
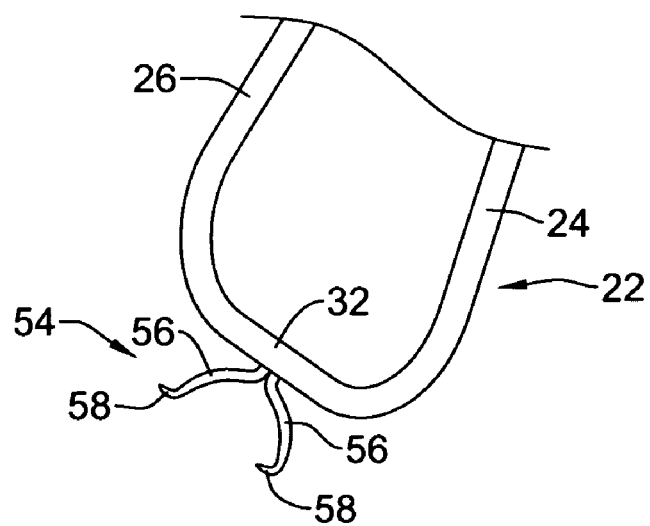
FIG. 5 is an enlarged view showing a portion of one of the filter loops in greater detail.

FIG. 5 is an enlarged view showing a portion of one of the filter loops 22 in greater detail. As can be seen in FIG. 5, one or more of the filter loops 22 can further optionally include an anchoring member 54 such as a needle, hook, barb, prong, or wedge that can be used to further secure the intravascular filter 10 to the inner wall of the blood vessel, if desired. In the illustrative embodiment of FIG. 5, for example, the anchoring member 54 may comprise a set of barbs 56 adapted to pierce and secure to the inner wall of the blood vessel during deployment. An end portion 58 of each barb 56 can be configured to pierce the endothelium layer of the blood vessel without protruding through the wall of the blood vessel.

Figure 6:
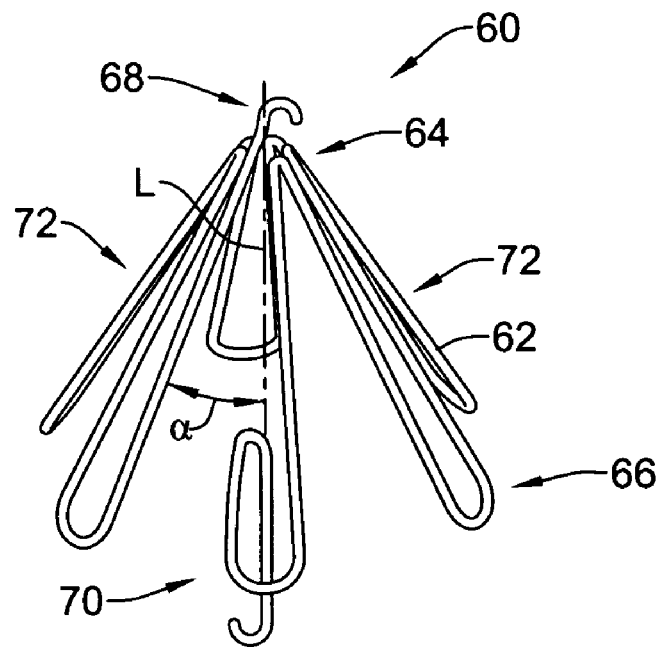
FIG. 6 is a perspective view of a single-wire intravascular filter in accordance with another illustrative embodiment of the present invention.

FIG. 6 is a perspective view of a single-wire intravascular filter 60 in accordance with another illustrative embodiment of the present invention. Intravascular filter 60 can be configured similar to the embodiment described above with respect to FIGS. 1-5, including a single filter wire 62 forming a substantially conical-shaped structure having an apex section 64, a base section 66, and a central longitudinal axis L. The filter wire 62 may extend from a first end section 68 of the intravascular filter 60 at or near the apex section 64 of the intravascular filter 60 to a second end section 70 thereof located at or near the base section 66 of the intravascular filter 60.

The filter 62 may further define a number of open-ended filter loops 72, each of which can be used to collect blood clots or other emboli within the blood stream. The filter loops 72 can be biased to slope outwardly at an angle α away from the central axis L of the intravascular filter 60, causing the filter loops 72 to exert a radial force on the inner wall of the blood vessel when deployed within the body. As with other embodiments described herein, the filter loops 72 can be configured to slope at the same angle α or at differing angles to facilitate insertion of the device in blood vessels of varying shape. In some embodiments, the filter wire 62 can assume a substantially vertical orientation (i.e. α 45°) to promote clot collection and lysing at or near the apex section 64 of the intravascular filter 60.

Figure 7:
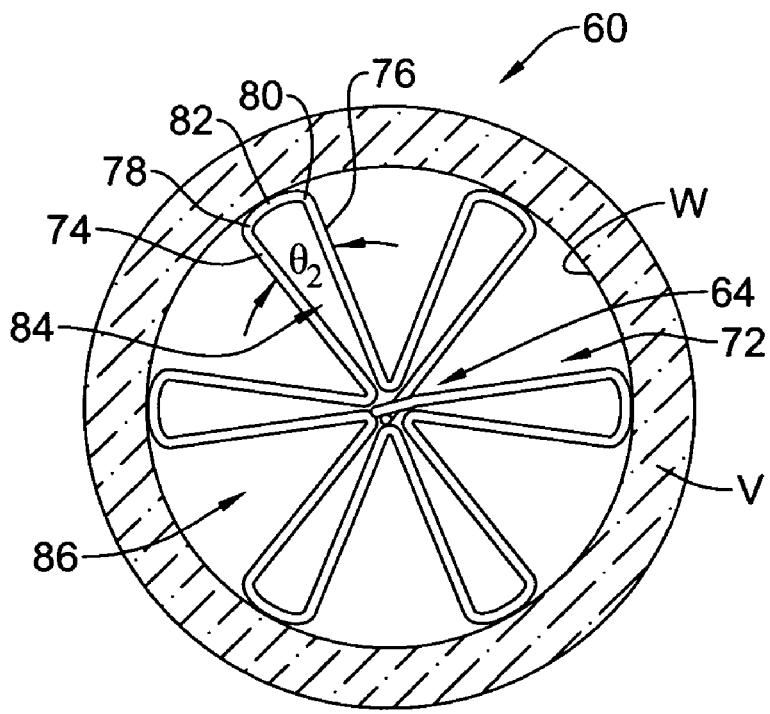
FIG. 7 is a top view showing the illustrative intravascular filter of FIG. 6 disposed within a blood vessel.

FIG. 7 is a top view showing the illustrative intravascular filter 60 of FIG. 6 disposed within a blood vessel. As can be seen in FIG. 7, each of the filter loops 72 may include a first section 74 and second section 76, each of which can extend outwardly away from the apex section 14 of the intravascular filter 10 in a direction towards the inner wall W of the blood vessel V. At locations 78 and 80, respectively, the first and second sections 74,76 of the filter loop 72 bend and orient in a direction aligned radially with the inner wall W of the blood vessel V, forming a third section 82 of the filter loop 72 configured to secure to the inner wall W of the blood vessel V. Together, the first, second, and third sections 74,76,82 of the filter loop 22 define an opening 84 through which blood can flow through the intravascular filter 60 substantially unimpeded.

As can be further seen in FIG. 7, the first and second sections 74,76 of each filter loop 72 can diverge from each other at an angle $\theta_2$ such that the opening 84 is greater towards the outer periphery of the intravascular filter 60 than at the apex section 64 thereof. In contrast to the intravascular filter 10 described above, however, the filter loops 72 in FIG. 7 are shown having a relatively narrow configuration (i.e. having a relatively small angle $\theta_2$), with the space 86 between adjacent filter loop 72 being relatively small in comparison to the opening 84 defined by the filter loop 72. Such configuration can be used, for example, to impart greater amount of flexibility to the intravascular filter 60, if desired. The number and configuration of filter loops 72 can, of course, be varied to alter the performance characteristics of the intravascular filter 60. Other features such as the anchoring members 54 described above can be further provided on one or more of the filter loops 72, if desired.

Figure 8:
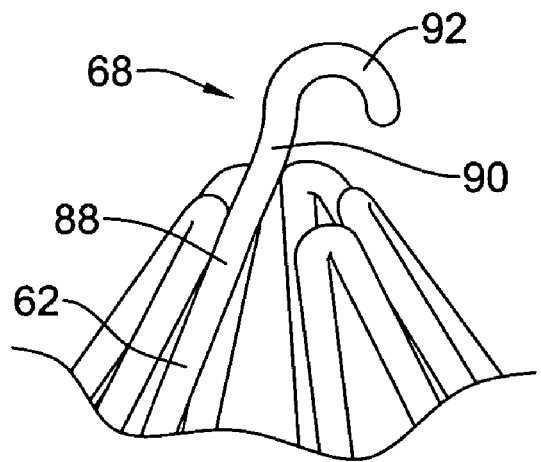
FIG. 8 is an enlarged view showing the first end section of the filter wire of FIG. 7 in greater detail.

FIG. 8 is an enlarged view showing the first end section 68 of the filter wire 62 in greater detail. As can be seen in FIG. 8, the first end section 68 may extend upwardly from an extended section 88 of one of the filter loops 72 wherein the filter wire 62 bends at location 90 and orients in an upward direction substantially collinear with the central longitudinal axis L of the intravascular filter 60. A hook 92 coupled to or formed integrally with the first end section 68 of the filter wire 62 can be used in conjunction with a retrieval device to retrieve the intravascular filter 60 via a jugular approach.

Figure 9:
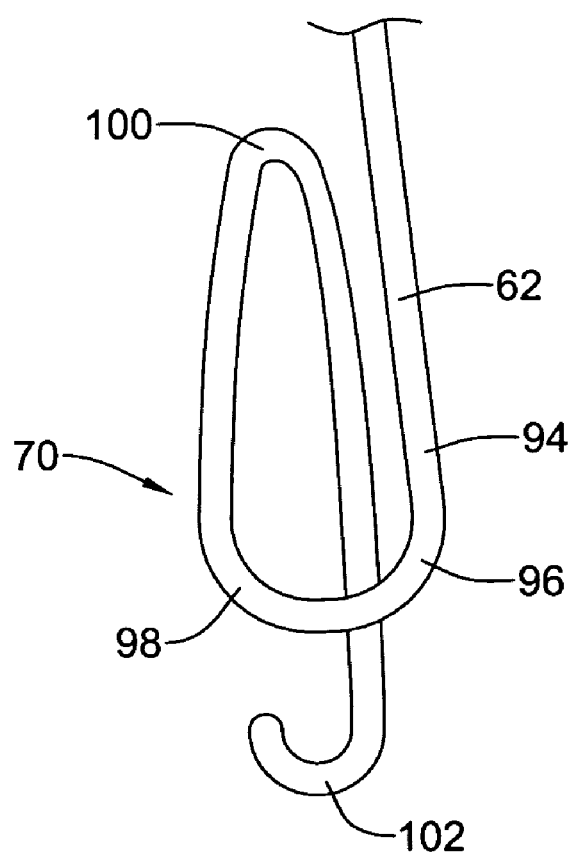
FIG. 9 is an enlarged view showing the second end section of the filter wire of FIG. 7 in greater detail.
Figure 10:
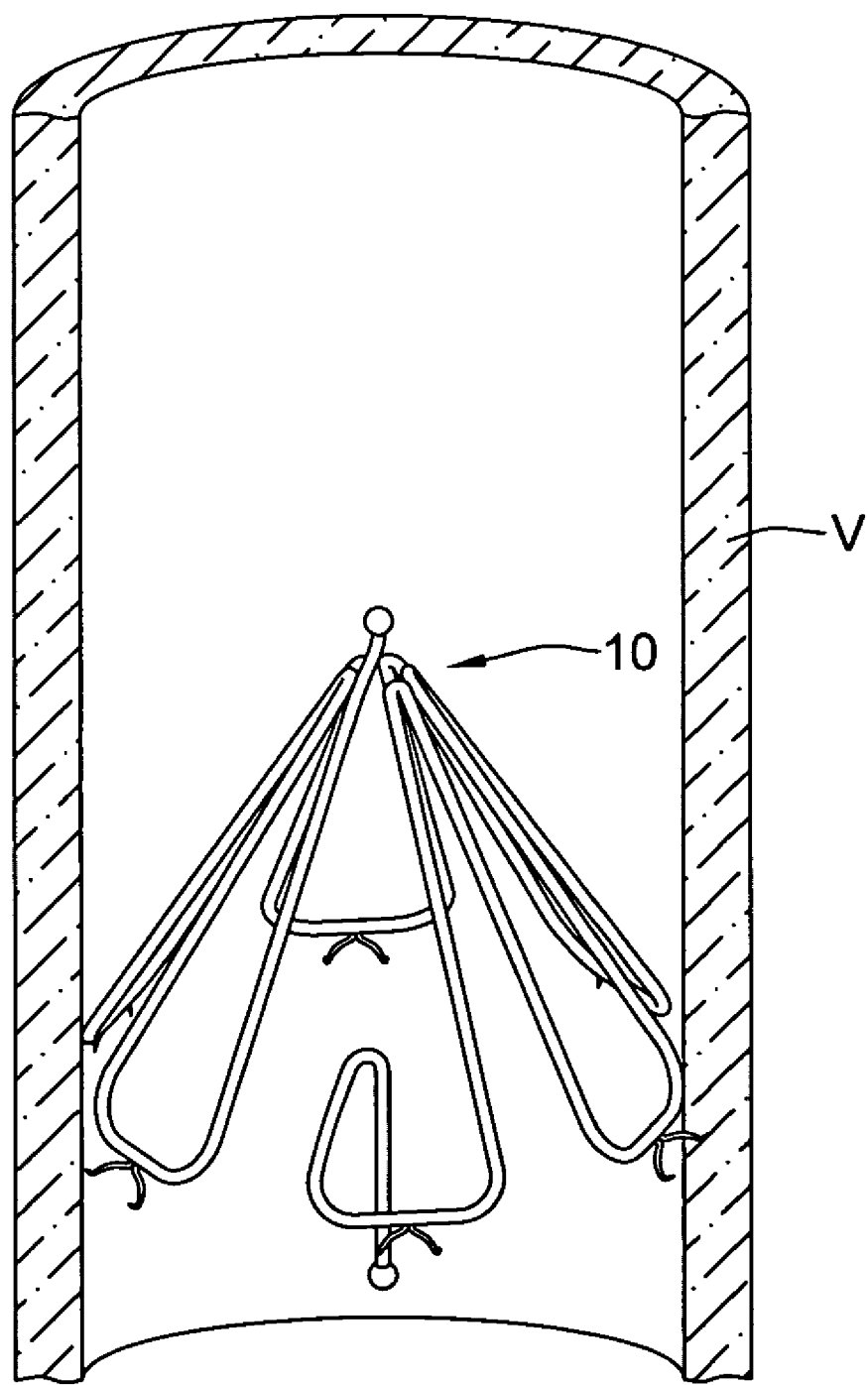
FIG. 10 is a partial cross-sectional view showing the intravascular filter of FIG. 1 implanted within a blood vessel.

In similar fashion, and as further shown in the enlarged view of FIG. 9, the second end section 70 of the filter wire 62 may extend downwardly from an extended portion 94 of one of the filter loops 72 wherein the filter wire 62 bends at locations 96,98,100 and orients in a downward direction substantially collinear with the central longitudinal axis L of the intravascular filter 60. A hook 102 coupled to or formed integrally with the second end section 70 of the filter wire 62 can be used in conjunction with a retrieval device to retrieve the intravascular filter 60 via a femoral approach.

Turning now to FIGS. 10-13, an illustrative method of retrieving an intravascular filter will now be described with respect to the illustrative intravascular filter 10 described above. In a first position depicted in FIG. 10, intravascular filter 10 is shown implanted along the inner wall W of a blood vessel V. In certain applications, for example, intravascular filter 10 may be implanted within a blood vessel V such as the inferior vena cava for the treatment of pulmonary embolisms or other cardiovascular events that can cause emboli to flow to the heart and lungs. It should be understood, however, that the intravascular filter 10 can be implanted in other locations of the body, if desired.

To deploy the intravascular filter 10, a delivery sheath pre-loaded with the collapsed filter 10 is advanced to the implantation site and withdrawn to expose the filter 10 within the blood vessel, causing the filter 10 to self-expand. Alternatively, it may be possible to deploy the intravascular filter 10 by advancing a delivery system with a pre-loaded single wire, which has been elongated within the delivery sheath. The single wire can then be advanced at the distal end of the delivery sheath to form the conical-shape of the intravascular filter 10 within the blood vessel.

Figure 11:
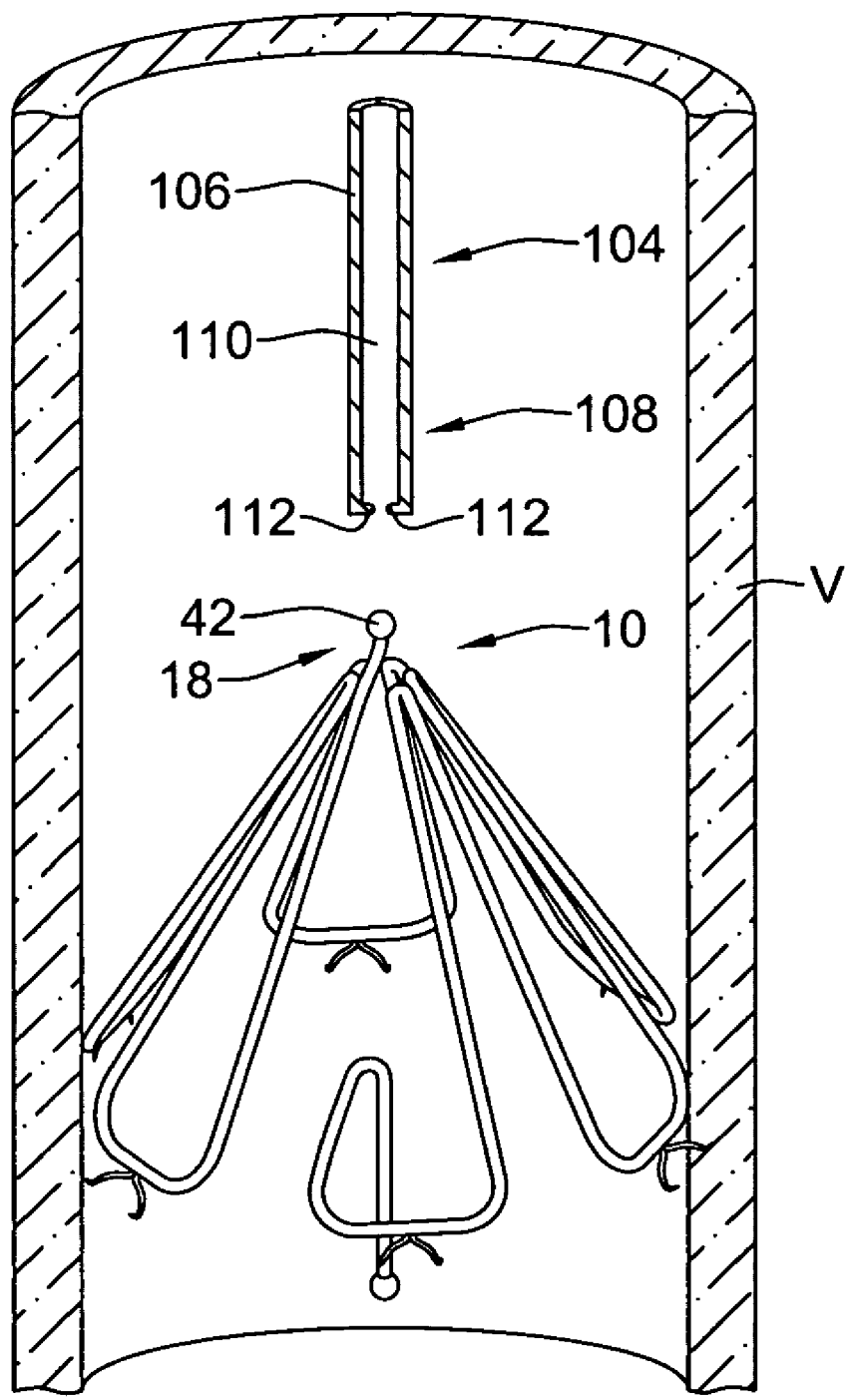
FIG. 11 is a partial cross-sectional view showing the advancement of a retrieval device to the site of the implanted intravascular filter of FIG. 10.

To retrieve the intravascular filter 10 from within the blood vessel V, a retrieval device 104 can be inserted percutaneously into the body and advanced intravenously to the site of the implanted intravascular filter 10, as shown, for example, in FIG. 11. The retrieval device 104 can include an elongated member 106 having a proximal section (not shown), a distal section 108, and an interior lumen 110 at least in part therethrough adapted to receive the rounded bead 42 of the filter wire 12. The proximal section of the retrieval device 104 can be manipulated from a location outside of the patient's body, allowing the physician to engage the distal section 108 against the intravascular filter 10. When this occurs, a set of inwardly projecting tabs or fingers 112 on the distal end of the retrieval device 104 can be configured to displace slightly, allowing passage of the rounded bead 42 into the interior lumen 110 of the retrieval device 104.

Figure 12:
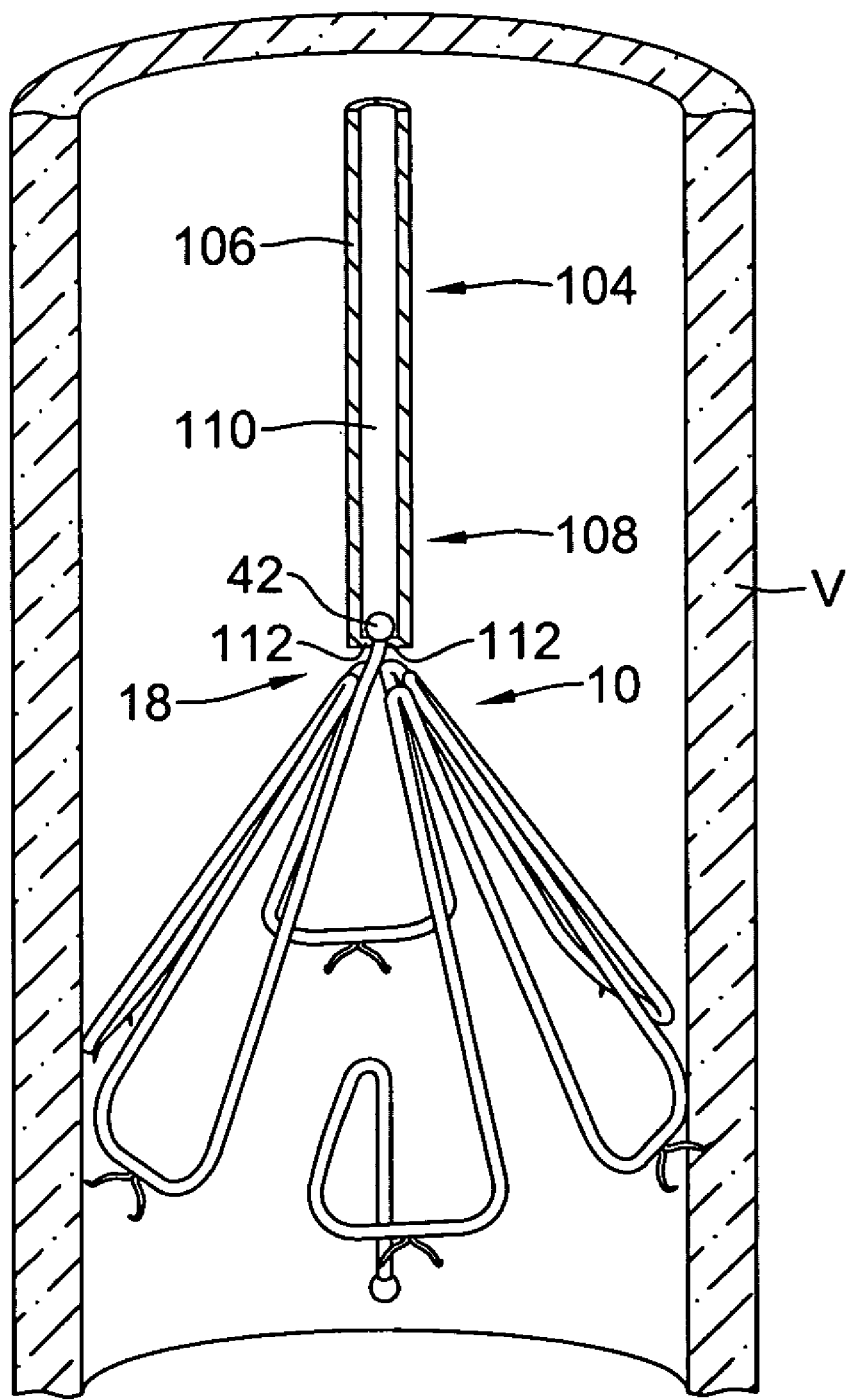
FIG. 12 is a partial cross-sectional view showing the retrieval device coupled to the intravascular filter.
Figure 13:
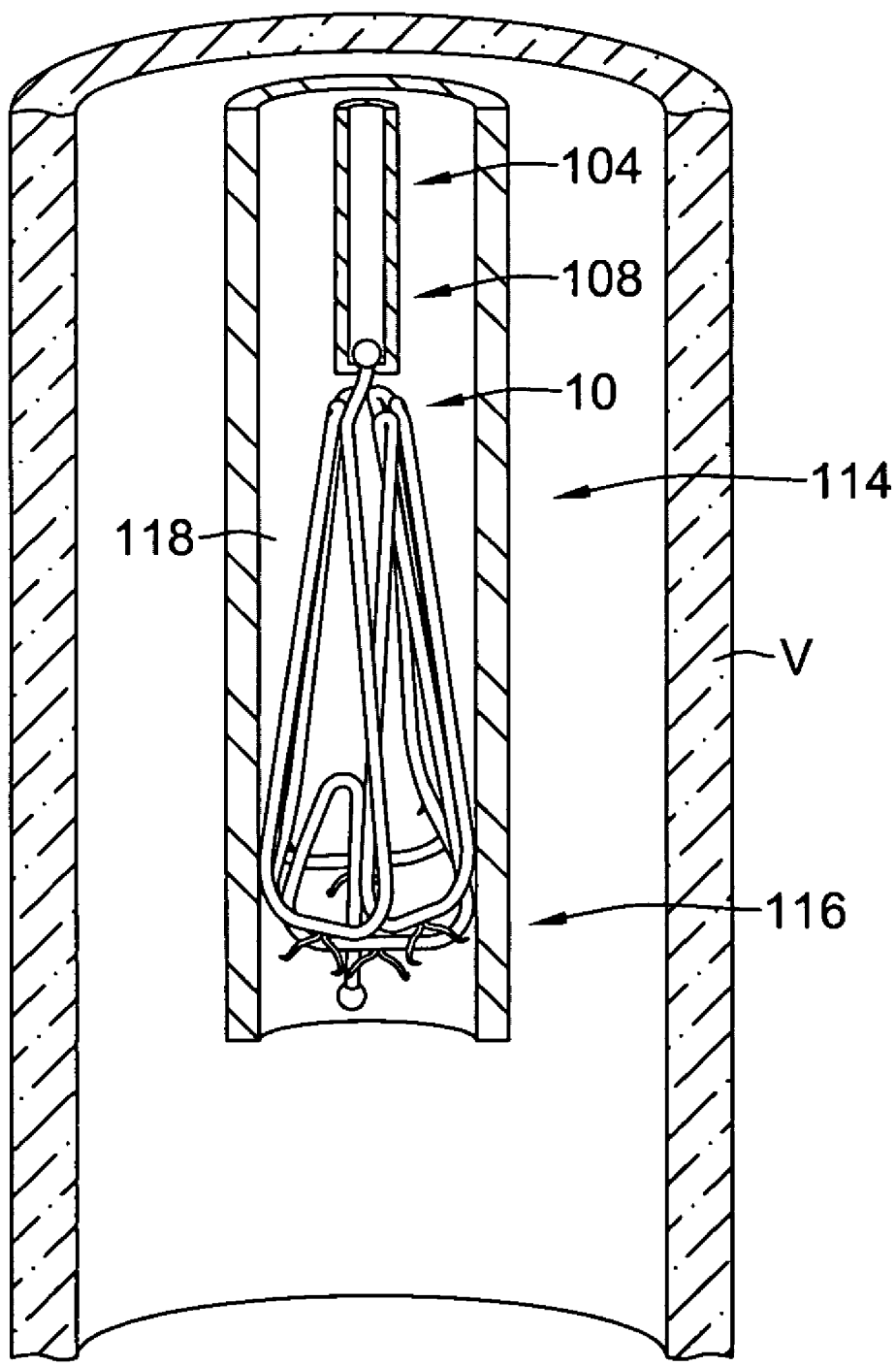
FIG. 13 is a partial cross-sectional view showing the intravascular filter collapsed within a retrieval sheath or catheter.

FIG. 12 is a partial cross-sectional view showing the retrieval device 104 coupled to the intravascular filter 10. As can be seen in FIG. 12, the inwardly projecting tabs or fingers 112 formed on the distal end of the retrieval device 104 can be configured to displace outwardly when advanced against the rounded bead 42, causing the rounded bead 42 to enter the interior lumen 110 of the retrieval device 104.

Once the retrieval device 104 is coupled to the rounded bead 42, a retrieval sheath 114 (see FIG. 13) having a proximal section (not shown), a distal section 116, and an interior lumen 118 adapted to collapse and receive the intravascular filter 10 therein can be inserted into the patient's body and advanced to the site of the intravascular filter 10. Once positioned adjacent the intravascular filter 10, the retrieval device 104 can then be withdrawn proximally while holding the retrieval sheath 114 stationary, causing the intravascular filter 10 to collapse at least in part within the interior lumen 118, as shown, for example, in FIG. 13. In an alternative embodiment, the retrieval device 104 can be held stationary while advancing the retrieval sheath 118 distally, similarly causing the intravascular filter 10 to collapse at least in part within the interior lumen 118. Once collapsed therein, the retrieval sheath 114, retrieval device 104, and intravascular filter 10 can then be removed from the patient's body or redeployed in a different location of the vasculature, as desired.

In an alternative method, retrieval of the intravascular filter 10 can be accomplished by withdrawing the captured end of the filter wire 12 into a retrieval sheath, causing the intravascular filter 10 to convert from its initial conical-shaped configuration into a straightened configuration within the retrieval sheath. To permit the intravascular filter 10 to assume a straightened configuration within the retrieval sheath, the single filter wire 12 can comprise a relatively elastic material that straightens in response to tension applied by the physician, but maintains its conical shape when deployed in the blood vessel.

Although the exemplary method depicted in FIGS. 10-13 shows the intravascular filter 10 being retrieved via a jugular approach (i.e. from a position above the intravascular filter 10), it should be understood that the intravascular filter 10 can also be retrieved using an alternative approach such as via one of the femoral arteries. In a femoral approach, for example, the retrieval device 104 can be inserted percutaneously into one of the femoral arteries (e.g. the left femoral artery) and advanced to the site of the implanted intravascular filter 10. As with a jugular approach, the distal section 108 of the retrieval device 104 can be engaged against the second end section 20 of the filter wire 12, causing the inwardly projecting tabs or fingers 112 to displace outwardly and permit the rounded bead 52 to enter the interior lumen 110 of the retrieval device 104. The intravascular filter 10 can then be collapsed and removed from the blood vessel using a retrieval sheath or catheter, similar to that described above with respect to FIG. 13.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. An intravascular filter, comprising:
a single filter wire defining a first end section, a second end section, and a plurality of open-ended filter loops adapted to collect blood clots contained within a blood vessel;
each of the plurality of filter loops sloping outwardly at an angle away from a central longitudinal axis of the intravascular filter and forming a conical-shaped structure having an apex section and a base section distal of the apex section, wherein each of the plurality of filter loops include a longitudinal length and a transverse length, wherein the longitudinal length is longer than the transverse length;
further comprising a retrieval member disposed on the first and second end sections of the filter wire;
wherein said retrieval member comprises a rounded bead;
wherein the first end section terminates proximal of the apex section and is oriented in a direction substantially collinear with the central longitudinal axis;
wherein the second end section terminates distal of the base section and is oriented in a direction substantially collinear with the central longitudinal axis.

2. The intravascular filter of claim 1, wherein each of said plurality of filter loops has a wide configuration.

3. The intravascular filter of claim 1, wherein each of said plurality of filter loops has a narrow configuration.

4. The intravascular filter of claim 1, wherein said filter wire is formed of a superelastic material.

5. The intravascular filter of claim 4, wherein said superelastic material comprises nickel-titanium alloy.

6. The intravascular filter of claim 1, further comprising an anchoring member provided on at least one of said plurality of filter loops.

7. The intravascular filter of claim 6, wherein said anchoring member comprises a barb.

8. The intravascular filter of claim 1, wherein said intravascular filter is retrievable via a jugular approach.

9. The intravascular filter of claim 1, wherein said intravascular filter is retrievable via a femoral approach.

10. The intravascular filter of claim 1, wherein said intravascular filter is a vena cava filter.

11. An intravascular filter, comprising:
a single filter wire defining a first end section, a second end section, and a plurality of discontinuos open-ended filter loops adapted to collect blood clots contained within a blood vessel, said first and second end sections being oriented in a direction substantially collinear with a central longitudinal axis of the intravascular filter;
wherein each of the plurality of filter loops slopes outwardly at an angle away from the central longitudinal axis to form a conical-shaped structure having an apex section and a base section, wherein each of the plurality of filter loops include a longitudinal length and a transverse length, wherein the length is longer than the transverse length; and
a rounded bead disposed on the first and second end sections of the filter wire;
wherein the first end section terminates proximal of the apex section and the second end section terminates distal of the base section.

* * * * *

UNITED STATES PATENT AND TRADEMARK OFFICE
CERTIFICATE OF CORRECTION

PATENT NO. : 7,794,472 B2
APPLICATION NO. : 10/916114
DATED : September 14, 2010
INVENTOR(S) : Tracee E. J. Eidenschink et al.

It is certified that error appears in the above-identified patent and that said Letters Patent is hereby corrected as shown below:

In the Claims:

Column 8, claim 11
Line 39 delete "discontinuous".

Line 49 delete "wherein the length is" and insert therefor -- wherein the longitudinal length is --.

Line 53 delete "wherein the first end section terminates" and insert therefor -- wherein the first longitudinal end section terminates --.

Signed and Sealed this

Sixteenth Day of November, 2010

David J. Kappos
*Director of the United States Patent and Trademark Office*